(12) United States Patent
Thaler et al.

(10) Patent No.: US 7,968,592 B2
(45) Date of Patent: Jun. 28, 2011

(54) 3-AMINOPYRROLIDONE DERIVATIVES

(75) Inventors: Florian Thaler, Bresso (IT); Cibele Maria Sabido David, Bresso (PT); Sara Maestroni, Bresso (IT); Luca Francesco Raveglia, Bresso (IT); Patricia Salvati, Bresso (IT)

(73) Assignee: Newron Pharmaceuticals S.p.A., Bresso (IT)

( * ) Notice: Subject to any disclaimer, the term of this patent is extended or adjusted under 35 U.S.C. 154(b) by 993 days.

(21) Appl. No.: 10/579,675

(22) PCT Filed: Nov. 16, 2004

(86) PCT No.: PCT/EP2004/012957
§ 371 (c)(1),
(2), (4) Date: Jul. 6, 2006

(87) PCT Pub. No.: WO2005/054190
PCT Pub. Date: Jun. 16, 2005

(65) Prior Publication Data
US 2007/0135410 A1    Jun. 14, 2007

(30) Foreign Application Priority Data
Nov. 21, 2003   (EP) .................................... 03026779

(51) Int. Cl.
| A61K 31/55 | (2006.01) |
| A61K 31/4412 | (2006.01) |
| A61K 31/4015 | (2006.01) |
| C07D 223/12 | (2006.01) |
| C07D 223/10 | (2006.01) |
| C07D 211/76 | (2006.01) |
| C07D 207/273 | (2006.01) |
| C07D 207/26 | (2006.01) |

(52) U.S. Cl. .................... 514/424; 514/349; 514/212.03; 540/527; 546/297; 548/550

(58) Field of Classification Search .................. 548/550; 546/297; 540/527; 514/212.03, 349, 424
See application file for complete search history.

(56) References Cited

FOREIGN PATENT DOCUMENTS

| WO | WO 97/05111 | 2/1997 |
| WO | WO 99/35123 | 7/1999 |
| WO | WO 99/35125 | 7/1999 |
| WO | WO 03/057219 | 7/2003 |

OTHER PUBLICATIONS

Suzuki et al. (JP 01204073 A, Aug. 16, 1989; see attached CAS Abstract and structure).*
Ragsdale et al. (Brain Research Reviews 1998, 26, 16-28).*
Leong et al. (Pain Medicine 2001, 2(3), 228-229).*
Sica, D.A. (The Journal of Clinical Hypertension 2006, 8(1), 53-56).*
Sabido-David (Expert. Opinion Investig. Drugs 2004, 13(10), 1249-1261).*
Priest et al. (PNAS 2007, 104(20), 8205-06).*
Brown et al. Environmental Health Perspectives 2005, 113(9), 1250-1256.*
Sydney-Smith's presentation: Neurodegenerative Disease, at the International Summit for Mental Health, Mar. 2009.*
Fischer et al. Neurodegenerative Diseases 2004, 1, 50-70.*
Database Chemcats Chemical Abstracts Service, Columbus, Ohio, US; XP002269487, Order No. CGX-0154580 & "Comgenex Product List", Jun. 26, 2003, Comgenex International, Inc, Monmouth Jct., NJ, 08852 USA.

* cited by examiner

Primary Examiner — Rebecca L Anderson
Assistant Examiner — Jason M Nolan
(74) Attorney, Agent, or Firm — Young & Thompson

(57) ABSTRACT

3-aminopyrrolidone compounds and pharmaceutically acceptable salts thereof that are active as sodium and/or calcium channel modulators and therefore useful in preventing, alleviating and curing a wide range of pathologies, including, but not limited to cardiovascular, inflammatory, ophthalmic, urologic, metabolic and gastrointestinal diseases.

2 Claims, No Drawings

3-AMINOPYRROLIDONE DERIVATIVES

This invention is related to 3-aminopyrrolidone derivatives and analogues of the following general formula I

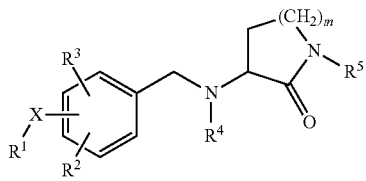

and pharmaceutically acceptable salts thereof, that are active as sodium and/or calcium channel modulators and therefore useful in preventing, alleviating and curing a wide range of pathologies, including, but not limited to, neurological, psychiatric, cardiovascular, inflammatory, ophthalmic, urologic, metabolic and gastrointestinal diseases, where the above mechanisms have been described as playing a pathological role.

BACKGROUND OF THE INVENTION

Chemical Background

WO97/05111 discloses N-(4-substituted-benzyl)-2-aminolactam derivatives of general formula II

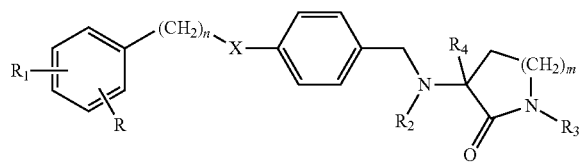

wherein:
m is zero, 1, 2 or 3; n is zero, 1, 2 or 3; X is O, S, $CH_2$ or NH; each of R and $R_1$ independently is hydrogen, $C_1$-$C_6$ alkyl, halogen, hydroxy, $C_1$-$C_4$ alkoxy or trifluoromethyl; each of $R_2$, $R_3$ and $R_4$ independently is hydrogen, $C_1$-$C_6$ alkyl optionally substituted by a hydroxy group, or $C_3$-$C_7$ cycloalkyl.

The compounds of the invention are active on the central nervous system (CNS) and can be used in therapy, for example as antiepileptics, in the treatment of Parkinson's disease and as neuroprotective agents, e.g. preventing or treating neuronal loss associated with stroke, ischemia, CNS trauma, hypoglycaemia or surgery and in treating or preventing neurodegenerative diseases such as Alzheimer's disease, amyotrophic lateral sclerosis, Down's syndrome or Huntington's disease; they can also be used as antidepressants, hypnotics and antispastic agents.

In WO 96/40679, WO 95/33719 and U.S. Pat. No. 3,714, 175 N-substituted pyrrolidone derivatives are claimed to be active as anticoagulants (Factor Xa), herbicidals and muscle relaxants, respectively.

In EP 0362941, N—OH substituted pyrrolidone derivatives are claimed to be active as anticonvulsants, muscle relaxants and in anti-neurodegenerative disorders.

Biological Background

It is well known that sodium channels play an important role in the neuronal network by transmitting electrical impulses rapidly throughout cells and cell networks, thereby coordinating higher processes ranging from locomotion to cognition. These channels are large transmembrane proteins, which are able to switch between different states to enable selective permeability for sodium ions. For this process an action potential is needed to depolarize the membrane, and hence these channels are voltage-gated. In the past few years a much better understanding of sodium channels and drugs interacting with them has been developed.

It has become clear that a number of drugs having an unknown mechanism of action actually act by modulating sodium channel conductance, including local anesthetics, class I antiarrhythmics and anticonvulsants. Neuronal sodium channel blockers have found application with their use in the treatment of epilepsy (phenyloin and carbamazepine), bipolar disorder (lamotrigine), preventing neurodegeneration, and in reducing neuropathic pain. Various anti-epileptic drugs that stabilize neuronal excitability are effective in neuropathic pain (gabapentin).

In addition, an increase in sodium channel expression or activity has also been observed in several models of inflammatory pain, suggesting a role of sodium channels in inflammatory pain.

Calcium channels are membrane-spanning, multi-subunit proteins that allow controlled entry of calcium ions into cells from the extracellular fluid. Commonly, calcium channels are voltage dependent and are referred to as voltage sensitive calcium channels (VSCC). VSCCs are found throughout the mammalian nervous system, where they regulate such varied activities as cellular excitability, transmitter release, intracellular metabolism, neurosecretory activity and gene expression. All "excitable" cells in animals, such as neurons of the central nervous system (CNS), peripheral nerve cells, and muscle cells, including those of skeletal muscles, cardiac muscles and venous and arterial smooth muscles, have voltage dependent calcium channels. Calcium channels have a central role in regulating intracellular calcium ions levels that are important for cell viability and function. Intracellular calcium ion concentrations are implicated in a number of vital processes in animals, such as neurotransmitter release, muscle contraction, pacemaker activity, and secretion of hormones. It is believed that calcium channels are relevant in certain disease states. A number of compounds useful in treating various cardiovascular diseases in mammals, including humans, are thought to exert their beneficial effects by modulating functions of voltage dependant calcium channels present in cardiac and/or vascular smooth muscle. Compounds with activity against calcium channels have also been implicated for the treatment of pain. In particular N-type calcium channels (Cav2.2), responsible for the regulation of neurotransmitters, are thought to play a significant role in nociceptive transmission, both due to their tissue distribution as well as from the results of several pharmacological studies. This hypothesis has been validated in the clinic by Zinocotide, a peptide derived from the venom of the marine snail, Conus Magus. A limitation in the therapeutic use of this peptide is that it has to be administered intrathecally in humans (Bowersox S. S. and Luther R. Toxicon, 1998, 36, 11, 1651-1658).

All together these findings indicate that compounds with sodium and/or calcium channel blockade have a high therapeutic potential in preventing, alleviating and curing a wide range of pathologies, including neurological, psychiatric, cardiovascular, urologic, metabolic and gastrointestinal diseases, where the above mechanisms have been described as playing a pathological role.

There are many papers and patents which describe sodium channel and/or calcium channel modulators or antagonists for the treatment or modulation of a plethora of disorders, such as their use as local anesthetics, antiarrhythmics, antiemetics, antimanic depressants, agents for the treatment of unipolar depression, cardiovascular diseases, urinary incontinence, diarrhea, inflammation, epilepsy, neurodegenerative conditions, nerve cell death, anticonvulsants, neuropathic pain, migraine, acute hyperalgesia and inflammation, renal disease, allergy, asthma, bronchospasm, dysmenorrhea, esophageal spasm, glaucoma, urinary tract disorders, gastrointestinal motility disorders, premature labour, obesity. A largely incomplete list is shown below.

An extensive and thorough prior art overview is reported in WO 03/057219 (and references therein); a further selection of prior art is reported in the following references: Alzheimer, C. Adv. Exp. Med. Biol. 2002, 513, 161-181; Vanegas, H.; Schaible, H. Pain 2000, 85, 9-18; U.S. Pat. No. 5,051,403; U.S. Pat. No. 5,587,454; U.S. Pat. No. 5,863,952; U.S. Pat. No. 6,011,035; U.S. Pat. No. 6,117,841; U.S. Pat. No. 6,362,174; U.S. Pat. No. 6,380,198; U.S. Pat. No. 6,420,383; U.S. Pat. No. 6,458,781; U.S. Pat. No. 6,472,530; U.S. Pat. No. 6,518,288; U.S. Pat. No. 6,521,647; WO 97/10210; WO 03/018561.

DESCRIPTION OF THE INVENTION

The present invention relates to the use of compounds of formula I

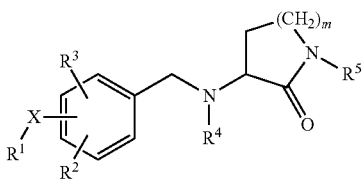

I wherein
m is an integer from 1 to 3
X is methylene, oxygen, sulphur or a $NR^6$ group;
$R^1$ is a straight or branched $C_1$-$C_8$ alkyl or $C_3$-$C_8$ alkenylene or $C_3$-$C_8$ alkynylene chain, optionally substituted with $CF_3$, phenyl, phenoxy or naphthyl, or phenyl, the aromatic rings optionally substituted by one or more $C_1$-$C_4$ alkyl, halogens, trifluoromethyl, hydroxy or $C_1$-$C_4$ alkoxy groups;
$R^2$, $R^3$ are independently hydrogen, a $C_1$-$C_3$ alkyl chain, halogen, trifluoromethyl, hydroxy or $C_1$-$C_4$ alkoxy groups;
$R^4$, $R^5$, $R^6$ are independently hydrogen or $C_1$-$C_6$ alkyl;
and the pharmaceutically acceptable salts thereof for the preparation of a medicament for the treatment of pain, migraine, cognitive disorders, inflammation, gastrointestinal tract disorders, disorders of the genito-urinary tract, ophthalmic diseases, obesity.

This invention is also related to the compounds of the general formula I
wherein m, X, $R^1$, $R^2$, $R^3$, $R^4$, $R^5$ and $R^6$ are as defined above with the proviso that:
when $R^1$ is phenyl, benzyl, 2-phenethyl or 3-phenpropyl optionally and independently substituted on the phenyl ring by one or two $C_1$-$C_6$ alkyl, halogen, hydroxy, $C_1$-$C_4$ alkoxy or trifluoromethyl; X is oxygen, sulphur, methylene or —NH—, at least one of $R^2$ and $R^3$ is other than hydrogen;

The disclaimed compounds are known from WO97/05111.
if m is 3, $R^1$—X 4-benzyloxy, $R^2$, $R^4$ and $R^5$ hydrogen then $R^3$ is other than 3-methoxy (CGX-0154772), and
if m is 3, $R^1$—X 3-benzyloxy, $R^2$, $R^4$ and $R^5$ hydrogen then $R^3$ is other than 4-methoxy (CGX-0154682).

The optional substituents $R^1$—X, $R^2$ and $R^3$ in the phenyl ring may be in any position.

The pharmaceutically acceptable salts of the compounds of formula I include acid addition salts with inorganic, e.g. hydrochloric, hydrobromic, sulphuric, and phosphoric acids or organic, e.g. acetic, propionic, benzoic, cinnamic, mandelic, salicylic, glycolic, lactic, oxalic, malic, maleic, malonic, fumaric, tartaric, citric, and the like.

Preferred use compounds of the invention are the compounds of formula I wherein m is 1 or 2, X is oxygen or methylene or NH or $NCH_3$, $R^1$ is $C_1$-$C_8$ alkyl chain, optionally substituted with $CF_3$, phenyl or phenoxy group, where the aromatic ring in $R^1$ is optionally substituted by one or two halogen or methoxy or trifluoromethyl groups, $R^2$ and $R^3$ are hydrogen, methyl, methoxy, fluorine, chlorine or bromine, $R^4$ and $R^5$ are hydrogen or methyl, halogen is chlorine or fluorine.

Examples of specific use compounds of the invention are:
3-(4-Butyloxy-benzylamino)-pyrrolidin-2-one;
3-[4-(4-trifluorobutyloxy)-benzylamino]-pyrrolidin-2-one;
3-(4-Pentyloxy-benzylamino)-pyrrolidin-2-one;
3-[4-(5-trifluoropentyloxy)-benzylamino]-pyrrolidin-2-one;
3-(4-Phenylethyl-benzylamino)-pyrrolidin-2-one;
3-(4-Benzyloxy-benzylamino)-pyrrolidin-2-one;
3-(4-Phenylbutoxy-benzylamino)-pyrrolidin-2-one;
3-(4-Phenylpentoxy-benzylamino)-pyrrolidin-2-one;
3-(4-Phenylallyloxy)-benzylamino-pyrrolidin-2-one;
3-(4-Phenoxyethoxy-benzylamino)-pyrrolidin-2-one;
3-[4-(Naphthalen-1-ylmethoxy)-benzylamino]-pyrrolidin-2-one;
3-(4-Pentyloxy-3-fluoro-benzylamino)-pyrrolidin-2-one;
3-(4-Pentyloxy-3-chloro-benzylamino)-pyrrolidin-2-one;
3-(4-Pentyloxy-3-bromo-benzylamino)-pyrrolidin-2-one;
3-(4-Pentyloxy-3-methoxy-benzylamino)-pyrrolidin-2-one;
3-(4-Pentyloxy-3-methyl-benzylamino)-pyrrolidin-2-one;
3-(4-Benzyloxy-3-fluoro-benzylamino)-pyrrolidin-2-one;
3-(4-Benzyloxy-3-bromo-benzylamino)-pyrrolidin-2-one;
3-(4-Benzyloxy-3-methoxy-benzylamino)-pyrrolidin-2-one;
3-(4-Benzyloxy-3-methyl-benzylamino)-pyrrolidin-2-one;
3-(4-Phenylpentoxy-2-chloro-benzylamino)-pyrrolidin-2-one;
3-(4-Phenylpentoxy-3-bromo-benzylamino)-pyrrolidin-2-one;
3-(4-Phenylpentoxy-3-methoxy-benzylamino)-pyrrolidin-2-one;
3-(4-Phenylpentoxy-3-methyl-benzylamino)-pyrrolidin-2-one;
3-(4-Phenylallyloxy-2-chloro-benzylamino)-pyrrolidin-2-one;
3-(4-Phenylallyloxy-3-fluoro-benzylamino)-pyrrolidin-2-one;
3-(4-Phenylallyloxy-3-bromo-benzylamino)-pyrrolidin-2-one;
3-(4-Phenylallyloxy-3-methoxy-benzylamino)-pyrrolidin-2-one;
3-(4-Phenylallyloxy-3-methyl-benzylamino)-pyrrolidin-2-one;

3-(4-Phenoxyethoxy-2-chloro-benzylamino)-pyrrolidin-2-one;
3-(4-Phenoxyethoxy-3-fluoro-benzylamino)-pyrrolidin-2-one;
3-(4-Phenoxyethoxy-3-bromo-benzylamino)-pyrrolidin-2-one;
3-(4-Phenoxyethoxy-3-methoxy-benzylamino)-pyrrolidin-2-one;
3-(4-Phenoxyethoxy-3-methyl-benzylamino)-pyrrolidin-2-one;
3-[4-(Naphthalen-1-ylmethoxy)-3-bromo-benzylamino]-pyrrolidin-2-one;
3-[4-(Naphthalen-1-ylmethoxy)-3-methoxy-benzylamino]-pyrrolidin-2-one;
3-[4-(Naphthalen-1-ylmethoxy)-3-methyl-benzyl amino]-pyrrolidin-2-one;
3-(4-Pentyloxy-3-bromo-5-methoxy-benzylamino)-pyrrolidin-2-one;
3-(4-Pentyloxy-3,5-dimethoxy-benzylamino)-pyrrolidin-2-one;
3-(4-Pentyloxy-3,5-dimethyl-benzylamino)-pyrrolidin-2-one;
3-(4-Benzyloxy-3-bromo-5-methoxy-benzylamino)-pyrrolidin-2-one;
3-(4-Benzyloxy-3,5-dimethoxy-benzylamino)-pyrrolidin-2-one;
3-(4-Benzyloxy-3,5-dimethyl-benzylamino)-pyrrolidin-2-one;
3-(4-Phenylallyloxy-3-bromo-5-methoxy-benzylamino)-pyrrolidin-2-one;
3-(4-Phenylallyloxy-3,5-dimethoxy-benzylamino)-pyrrolidin-2-one;
3-(4-Phenylallyloxy-3,5-dimethyl-benzylamino)-pyrrolidin-2-one;
3-(4-Phenylpentoxy-3-bromo-5-methoxy-benzylamino)-pyrrolidin-2-one;
3-(4-Phenylpentoxy-3,5-dimethoxy-benzylamino)-pyrrolidin-2-one;
3-(4-Phenylpentoxy-3,5-dimethyl-benzylamino)-pyrrolidin-2-one;
3-(4-Phenoxyethoxy-3-bromo-5-methoxy-benzylamino)-pyrrolidin-2-one;
3-(4-Phenoxyethoxy-3,5-dimethoxy-benzylamino)-pyrrolidin-2-one;
3-(4-Phenoxyethoxy-3,5-dimethyl-benzylamino)-pyrrolidin-2-one;
3-[4-(Naphthalen-1-ylmethoxy)-2-chloro-5-methoxy-benzylamino]-pyrrolidin-2-one;
3-[4-(Naphthalen-1-ylmethoxy)-3-fluoro-5-methoxy-benzylamino]-pyrrolidin-2-one;
3-[4-(Naphthalen-1-ylmethoxy)-3-bromo-5-methoxy-benzylamino]-pyrrolidin-2-one;
3-[4-(Naphthalen-1-ylmethoxy)-3,5-dimethoxy-benzylamino]-pyrrolidin-2-one;
3-[4-(Naphthalen-1-ylmethoxy)-3,5-dimethyl-benzylamino]-pyrrolidin-2-one;
3-[4-(2-Fluorobenzyloxy)-benzylamino]-pyrrolidin-2-one;
3-[4-(2-Fluorobenzyloxy)-benzylamino]-N-methylpyrrolidin-2-one;
3-[4-(2-triFluoromethyl-benzyloxy)-benzylamino]-pyrrolidin-2-one;
3-[4-(2-Chlorobenzyloxy)-benzylamino]-pyrrolidin-2-one;
3-[4-(2-Methoxybenzyloxy)-benzylamino]-pyrrolidin-2-one;
3-[4-(3-Fluorobenzyloxy)-benzylamino]-pyrrolidin-2-one;
3-[4-(3-Fluorobenzyloxy)-benzylamino]-N-methylpyrrolidin-2-one;
3-{N-[4-(3-Fluorobenzyloxy)-benzyl]-N-methyl}-amino-pyrrolidin-2-one;
3-[4-(3-triFluoromethyl-benzyloxy)-benzylamino]-pyrrolidin-2-one;
3-[4-(3-Chlorobenzyloxy)-benzylamino]-pyrrolidin-2-one;
3-[4-(3-Methoxybenzyloxy)-benzylamino]-pyrrolidin-2-one;
3-[4-(3-Methoxybenzyloxy)-benzylamino]-N-methylpyrrolidin-2-one;
3-[4-(4-Fluorobenzyloxy)-benzylamino]-pyrrolidin-2-one;
3-[4-(4-Chlorobenzyloxy)-benzylamino]-pyrrolidin-2-one;
3-[4-(4-Methoxybenzyloxy)-benzylamino]-pyrrolidin-2-one;
3-[4-(4-triFluoromethyl-benzyloxy)-benzylamino]-pyrrolidin-2-one;
3-[4-(2,3-diChlorobenzyloxy)-benzylamino]-pyrrolidin-2-one;
3-[4-(3,4-diChlorobenzyloxy)-benzylamino]-pyrrolidin-2-one;
3-[4-(3,4-diMethoxybenzyloxy)-benzylamino]-pyrrolidin-2-one;
3-[4-(3,5-diMethoxybenzyloxy)-benzylamino]-pyrrolidin-2-one;
3-[4-(3,5-diMethoxybenzyloxy)-benzylamino]-N-methylpyrrolidin-2-one;
3-[4-(3,5-diMethoxyphenyl)-pentoxy]-benzylamino-pyrrolidin-2-one;
3-[4-(2-Fluorobenzyloxy)-3-methyl-benzylamino]-pyrrolidin-2-one;
3-[4-(2-triFluoromethyl-benzyloxy)-3-methyl-benzylamino]-pyrrolidin-2-one;
3-[4-(3-Fluorobenzyloxy)-3-methyl-benzylamino]-pyrrolidin-2-one;
3-{[4-(3-Fluorobenzyloxy)-3-methyl-benzyl]-N-methylamino}-pyrrolidin-2-one;
3-[4-(3-triFluoromethyl-benzyloxy)-3-methyl-benzylamino]-pyrrolidin-2-one;
3-[4-(3-Chlorobenzyloxy)-3-methyl-benzylamino]-pyrrolidin-2-one;
3-{[4-(3-Chlorobenzyloxy)-3-methyl-benzyl]-N-methylamino}-pyrrolidin-2-one;
3-[4-(3-Bromobenzyloxy)-3-methyl-benzylamino]-pyrrolidin-2-one;
3-{[4-(3-Bromobenzyloxy)-3-methyl-benzyl]-N-methylamino}-pyrrolidin-2-one;
3-[4-(4-triFluoromethyl-benzyloxy)-2-chloro-benzylamino]-pyrrolidin-2-one;
3-[4-(4-Fluorobenzyloxy)-3-methyl-benzylamino]-pyrrolidin-2-one;
3-[4-(4-triFluoromethyl-benzyloxy)-3-fluoro-benzylamino]-pyrrolidin-2-one;
3-[4-(4-triFluoromethyl-benzyloxy)-3-bromo-benzylamino]-pyrrolidin-2-one;
3-[4-(4-triFluoromethyl-benzyloxy)-3-methoxy-benzylamino]-pyrrolidin-2-one;
3-[4-(4-triFluoromethyl-benzyloxy)-3-methyl-benzylamino]-pyrrolidin-2-one;
3-[4-(4-Chlorobenzyloxy)-3-methyl-benzylamino]-pyrrolidin-2-one;
3-[4-(4-triFluoromethyl-benzyloxy)-3-bromo-5-methoxy-benzylamino]-pyrrolidin-2-one;
3-[4-(4-triFluoromethyl-benzyloxy)-3,5-dimethoxy-benzylamino]-pyrrolidin-2-one;
3-[4-(4-triFluoromethyl-benzyloxy)-3,5-dimethyl-benzylamino]-pyrrolidin-2-one;
3-[4-(3,4-diChlorobenzyloxy)-2-chloro-benzylamino]-pyrrolidin-2-one;

3-[4-(3,4-diChlorobenzyloxy)-3-fluoro-benzylamino]-pyrrolidin-2-one;
3-[4-(3,4-diChlorobenzyloxy)-3-bromo-benzylamino]-pyrrolidin-2-one;
3-[4-(3,4-diChlorobenzyloxy)-3-methoxy-benzylamino]-pyrrolidin-2-one;
3-[4-(3,4-diChlorobenzyloxy)-3-methyl-benzylamino]-pyrrolidin-2-one;
3-[4-(3,5-diMethoxybenzyloxy)-2-chloro-benzylamino]-pyrrolidin-2-one;
3-[4-(3,5-diMethoxybenzyloxy)-3-fluoro-benzylamino]-pyrrolidin-2-one;
3-[4-(3,5-diMethoxybenzyloxy)-3-bromo-benzylamino]-pyrrolidin-2-one;
3-[4-(3,5-diMethoxybenzyloxy)-3-methoxy-benzylamino]-pyrrolidin-2-one;
3-[4-(3,5-diMethoxybenzyloxy)-3-methyl-benzylamino]-pyrrolidin-2-one;
3-[4-(3,4-diChlorobenzyloxy)-3,5-dimethoxy-benzylamino]-pyrrolidin-2-one;
3-[4-(3,4-diChlorobenzyloxy)-3,5-dimethyl-benzylamino]-pyrrolidin-2-one;
3-[4-(3,5-diChlorobenzyloxy)-3-bromo-5-methoxy-benzylamino]-pyrrolidin-2-one;
3-[4-(3,5-diMethoxybenzyloxy)-3-bromo-5-methoxy-benzylamino]-pyrrolidin-2-one;
3-[4-(3,5-diMethoxybenzyloxy)-3,5-dimethoxy-benzylamino]-pyrrolidin-2-one;
3-[4-(3,5-diMethoxyphenyl)-allyloxy)-3,5-dimethoxy-benzylamino]-pyrrolidin-2-one.
3-(4-Benzyloxy-benzylamino)-piperidin-2-one;
3-(4-Benzyloxy-benzylamino)-azepan-2-one;
3-[4-(2-Fluorobenzyloxy)-benzylamino]-piperidin-2-one;
3-[4-(2-Fluorobenzyloxy)-benzylamino]-azepan-2-one;
3-[4-(2-Chlorobenzyloxy)-benzylamino]-piperidin-2-one;
3-[4-(2-Chlorobenzyloxy)-benzylamino]-azepan-2-one;
3-[4-(3-Fluorobenzyloxy)-benzylamino]-piperidin-2-one;
3-[4-(3-Fluorobenzyloxy)-benzylamino]-azepan-2-one;
3-[4-(4-Fluorobenzyloxy)-benzylamino]-piperidin-2-one;
3-[4-(4-Fluorobenzyloxy)-benzylamino]-azepan-2-one;
3-[4-(2-Chlorobenzylamino)-benzylamino]-piperidin-2-one;
3-[4-(2-Chlorobenzylamino)-benzylamino]-azepan-2-one;
3-{4-[(2-Chlorobenzyl)methylamino]-benzylamino}-piperidin-2-one;
3-{4-[(2-Chlorobenzyl)methylamino]-benzylamino}-azepan-2-one;
3-(4-Phenoxybenzylamino)-pyrrolidin-2-one;
or pharmaceutically acceptable salts thereof.

The compounds of the invention and the salts thereof can be obtained by a process comprising:
a) reaction of compounds of formula II

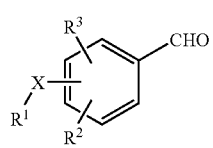

wherein $R^1$, $R^2$, $R^3$ and X are as defined above
with compounds of formula III, in the presence of a reducing agent

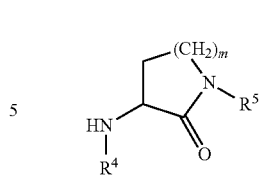

wherein m and $R^5$ are as defined previously thus obtaining a compound of formula I; or
b) reaction of compounds of formula IV

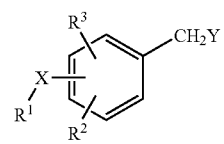

wherein $R^1$, $R^2$, $R^3$ and X are as defined above and Y is a halogen atom or a O-EWG group, where the EWG means an electron withdrawing group, like e.g. mesyl, tosyl or trifluoroacetyl groups, able to transform the oxygen which they are linked to, in a good leaving group
with compounds of formula III thus obtaining a compound of formula I; or
c) reacting of a compound of formula V

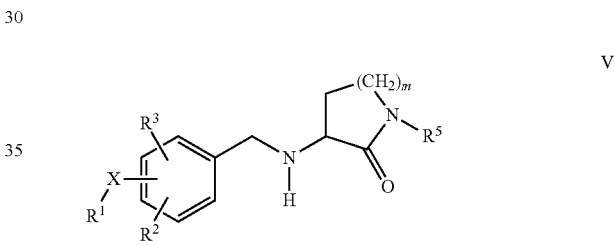

wherein $R^1$, $R^2$, $R^3$, $R^5$, X and m are as defined above, with compounds of formula VI or VII

    VI

    VII wherein Y is as defined above; $R^4$ is as above defined and $R^7$ is hydrogen or $C_1$-$C_5$ alkyl; and, if desired, converting a compound of the invention into another compound of the invention and/or, if desired, converting a compound of the invention into a pharmaceutically acceptable salt and/or, if desired, converting a salt into a free compound and/or, if desired, separating a mixture of isomers of compounds of the invention into a single isomer.

Compounds II, III, IV, VI and VII are commercially available compounds or are prepared from commercially available compounds using well-known methods.

The reactions of compounds of formula II with compounds of formula III and of compounds of formula V with compounds of formula VII to give the compounds of formula I is a reductive amination reaction which can be carried out according to known methods. According to a preferred embodiment of the invention, it may be performed under nitrogen atmosphere, in a suitable organic solvent, such as an alcohol, e.g. a lower alkanol, in particular methanol, or in acetonitrile, or in tetrahydrofuran, at a temperature ranging from about 0° C. to about 70° C., in the presence of a reducing agent, the most appropriate being sodium borohydride or sodium cyanoborohydride. Occasionally Titanium IV isopropylate and molecular sieves can be added to the reaction mixture for facilitating the reaction.

In a compound of formula IV and VI the halogen is preferably bromine or iodine. The alkylation reactions of a compound of formula IV with a compound of formula III and of a compound of formula V with a compound of formula VI can be carried out in a suitable organic solvent, such as an alcohol, e.g. methanol, ethanol or isopropanol, in particular in ethanol, at a temperature ranging from about 0° C. to about 50° C.

When in the compounds of the present invention and in the intermediate-products thereof, groups are present, which need to be protected before submitting them to the above illustrated reactions, they may be protected before being reacted and then deprotected according to well-known methods.

Pharmacology

The compounds of the invention display affinities for the calcium and/or sodium channel binding sites as demonstrated using selective radioligands in in vitro binding studies.

The compounds according to the invention are blockers of the voltage dependent sodium channels and/or calcium channels. These compounds therefore displace 3H-batrachotoxin (BTX) with a high affinity from the binding site on the sodium channel, with $IC_{50}$ in the low µM or sub µM range. Similarly the compounds displace 3H-nitrendipine from the binding site in the calcium channel, with $IC_{50}$ in the low µM or most usually in the sub µM range as well as inhibiting calcium influx induced through calcium channels via cellular depolarisation.

Such substances exhibit "use-dependency" when the sodium channels are blocked i.e. maximum blockage of the sodium channels is only achieved after repeated stimulation of the sodium channel. Consequently, the substances preferably bind to sodium channels which are multiply activated. As a result the substances are capable of activity preferentially in those regions of the body which are pathologically overstimulated, as illustrated by patch-clamp experiments (W. A. Catteral, Trends Pharmacol. Sci., 8, 57-65; 1987) which show that the compounds according to the invention block the electrically stimulated sodium channel in a "use-dependent" manner.

The compounds of the invention are voltage dependent blockers of the calcium and/or sodium channels as demonstrated by fluorescence calcium influx assay and electrophysiological studies.

The N-type calcium channel modulating activity of the 3-aminopyrrolidone derivatives of general formula I was measured through a fluorescence based calcium influx assay.

The sodium channel modulating activity of the 3-aminopyrrolidone derivatives of general formula I was measured through electrophysiological assays using the two electrodes voltage clamp (TEVC) technique in isolated *Xenopus* oocytes expressing the Na channel Nav1.3.

As a consequence of these mechanisms the compounds of the invention are active in vivo when orally administered in the range of 0.1 to 100 mg/kg in animal models such as the formalin model of persistent pain and the carragenan model of inflammation.

In view of the above described mechanisms of action, the compounds of the present invention are useful in the treatment or prevention of neuropathic pain. Neuropathic pain syndromes include, and are not limited to: diabetic neuropathy; sciatica; non-specific lower back pain; multiple sclerosis pain; fibromyalgia; HIV-related neuropathy; neuralgia, such as post-herpetic neuralgia and trigeminal neuralgia; and pain resulting from physical trauma, amputation, cancer, toxins or chronic inflammatory conditions.

Compounds of the invention are also useful for the treatment of chronic pain. Chronic pain includes, and is not limited to, chronic pain caused by inflammation or an inflammatory-related condition, ostheoarthritis, rheumatoid arthritis, acute injury or trauma, upper back pain or lower back pain (resulting from systematic, regional or primary spine disease (such as radiculopathy), bone pain, pelvic pain, spinal cord injury-associated pain, cardiac chest pain, non-cardiac chest pain, central post-stroke pain, myofascial pain, cancer pain, geriatric pain or pain caused by headache, temporomandibular joint syndrome, gout, fibrosis or thoracic outlet syndromes. In particular rheumatoid arthritis and ostheoarthritis.

Compounds of the invention are also useful in the treatment of acute pain (caused by acute injury, illness, sports-medicine injuries, carpal tunnel syndrome, burns, musculoskeletal sprains and strains, musculotendinous strain, cervicobrachial pain syndromes, dyspepsis, gastric ulcer, duodenal ulcer, dysmenorrhea, endometriosis or surgery (such as open heart or bypass surgery), post operative pain, kidney stone pain, gallbladder pain, gallstone pain, obstetric pain or dental pain.

Compounds of the invention are also useful in the treatment of migraine, such as tension type headache, transformed migraine or evolutive headache, cluster headache, as well as secondary headache disorders, such as the ones derived from infections, metabolic disorders or other systemic illnesses and other acute headaches, paroxysmal hemicrania and the like, resulting from a worsening of the above mentioned primary and secondary headaches.

Compounds of the invention are also useful for the treatment of cognitive disorders.

Compounds of the invention are also useful for the treatment of psychiatric disorders. Psychiatric disorders include, and are not limited to, bipolar disorder (such as bipolar disorder type I, bipolar disorder type II), cyclothymic disorder, rapid cycling, ultradian cycling, mania, hypomania, schizophrenia, schizophreniform disorders, schizoaffective disorders, delusional disorders, brief psychotic disorders, shared psychotic disorders, psychotic disorder due to a general medical condition, substance-induced psychotic disorders or a psychotic disorder not otherwise specified, anxiety disorders and moreover in smoke and drug addiction. In particular bipolar disorders, psychosis and addiction.

Compounds of the invention are also useful in the treatment of peripheral diseases such as tinnitus.

Compounds of the invention inhibit inflammatory processes affecting all body systems. Therefore are useful in the treatment of inflammatory processes of the muscular-skeletal system of which the following is a list of examples but it is not comprehensive of all target disorders: arthritic conditions such as alkylosing spondylitis, cervical arthritis, fibromyalgia, gut, juvenile rheumatoid arthritis, lumbosacral arthritis, osteoarthritis, osteoporosis, psoriatic arthritis, rheumatic disease; disorders affecting skin and related tissues: eczema, psoriasis, dermatitis and inflammatory conditions such as sunburn; disorders of the respiratory system: asthma, allergic rhinitis and respiratory distress syndrome, lung disorders in which inflammation is involved such as asthma and bronchitis; chronic obstructive pulmonary disease; disorders of the immune and endocrinological systems: periarthritis nodosa, thyroiditis, aplastic anaemia, sclerodoma, myasthenia gravis, multiple sclerosis, sarcoidosis, nephritic syndrome, Bechet's syndrome, polymyositis, gingivitis.

Compounds of the invention are also useful in the treatment of gastrointestinal (GI) tract disorders such as inflammatory bowel disorders including but not limited to ulcerative colitis, Crohn's disease, ileitis, proctitis, celiac disease, enteropathies, microscopic or collagenous colitis, eosinophilic gastroenteritis, or pouchitis resulting after proctocolectomy and post ileonatal anastomosis, and irritable bowel syndrome including any disorders associated with abdominal pain and/or abdominal discomfort such as pylorospasm, nervous indigestion, spastic colon, spastic colitis, spastic bowel, intestinal neurosis, functional colitis, mucous colitis, laxative colitis and functional dyspepsia; but also for treatment of atrophic gastritis, gastritis varialoforme, ulcerative colitis, peptic ulceration, pyresis, and other damage to the GI tract, for example, by *Helicobacter pylori*, gastroesophageal reflux disease, gastroparesis, such as diabetic gastroparesis; and other functional bowel disorders, such as non-ulcerative dyspepsia (NUD); emesis, diarrhea, and visceral inflammation.

Compounds of the invention are also useful in the treatment of disorders of the genito-urinary tract such as overactive bladder, prostatitis (chronic bacterial and chronic non-bacterial prostatitis), prostadynia, interstitial cystitis, urinary incontinence and benign prostatic hyperplasia, annexities, pelvic inflammation, bartolinities and vaginitis. In particular overactive bladder and urinary incontinence.

Compounds of the invention are also useful in the treatment of ophthalmic diseases such as retinitis, retinopathies, uveitis and acute injury to the eye tissue, macular degeneration or glaucoma, conjunctivitis.

Compounds of the invention are also useful in the treatment of obesity.

Compounds of the invention are also useful for the treatment of all other conditions mediated by the inhibition of voltage gated sodium channels and/or voltage gated calcium channels.

It will be appreciated that the compounds of the invention may advantageously be used in conjunction with one or more other therapeutic agents. Examples of suitable agents for adjunctive therapy include a $5HT_{1B/1D}$ agonist, such as a triptan (e.g. sumatriptan or naratriptan); an adenosine A1 agonist; an EP ligand; an NMDA modulator, such as a glycine antagonist; a substance P antagonist (e.g. an NK1 antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptiline); a neurone stabilising antiepileptic drug; a monoaminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumor necrosis factor alpha; an antibody therapy, such as monoclonal antibody therapy; an antiviral agent, such as a nucleoside inhibitor (e.g. lamivudine) or an immune system modulator (e.g. interferon); an analgesic, such as a cyclooxygenase-2 inhibitor; a local anaesthetic; a stimulant, including caffeine; an H2-antagonist (e.g. ranitidine); a proton pump inhibitor (e.g. omeprazole); an antacid (e.g. aluminium or magnesium hydroxide; an antiflatulent (e.g. semethicone); a decongestant (e.g. phenylephrine, phenylpropanolamine, pseudoephedrine, oxymetazoline, epinephrine, naphazoline, xylometazoline, propylhexedrine, or levo-desoxyephedrine, naphazoline, xylometazoline, propylhexedrine, or levo-desoxyephedrine); antitussive (e.g. codeine, hydrocodone, carmiphen, carbetapentane, or dextramethorphan); a diuretic; or a sedating or non-sedating antihistamine. It is to be understood that the present invention covers the use of a compound of formula (I) or a pharmaceutically acceptable salt thereof in combination with one or more therapeutic agents.

The compounds of the present invention are useful in human and veterinary medicine. It is to be understood that reference to treatment includes both treatments of established symptoms and prophylactic treatment, unless explicitly stated otherwise.

The 3-aminopyrrolidone derivatives of formula I as above defined can be administered as the "active ingredient" of a pharmaceutically acceptable composition which can be prepared by conventional procedures, for instance by mixing the active ingredient with pharmaceutically acceptable, therapeutically inert organic and/or inorganic carrier materials.

The composition comprising the above defined 3-aminopyrrolidone derivatives can be administered in a variety forms, e.g. orally, in the form of tablets, troches, capsules, sugar or film coated tablets, liquid solutions, emulsions or suspensions; rectally, in the form of suppositories; parenterally, e.g. by intramuscular or intravenous injection or infusion; and transdermally.

Suitable pharmaceutically acceptable, therapeutically inert organic and/or inorganic carrier materials useful in the preparation of such composition include, for example, water, gelatin, gum arabic, lactose, starch, cellulose, magnesium stearate, talc, vegetable oils, polyalkyleneglycols and the like. The composition comprising the 3-aminopyrrolidone derivatives of formula I as above defined can be sterilized and may contain further well known components, such as, for example, preservatives, stabilizers, wetting or emulsifying agents, e.g. paraffin oil, mannide monooleate, salts to adjust osmotic pressure, buffers and the like.

For example, the solid oral forms may contain, together with the active ingredient, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disgregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The oral formulations comprise sustained release formulations that can be prepared in conventional manner, for instance by applying an enteric coating to tablets and granules.

The liquid dispersion for oral administration may be e.g. syrups, emulsions and suspensions.

The syrups may contain as carrier, for example, saccharose or saccharose with glycerine and/or mannitol and/or sorbitol.

Suspensions and emulsions may contain as a carrier, for example, a natural gum, agar, sodium alginate, pectin, methylcellulose, carboxymethyl-cellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusion may contain as carrier, for example, sterile water or preferably they may be in the form of sterile, aqueous, isotonic saline solutions.

The suppositories may contain, together with the active ingredient, a pharmaceutically acceptable carrier, e.g. cocoa butter, polyethylene glycol, a polyoxyethylene sorbitan fatty acid ester surfactants or lecithin.

Suitable treatment is given 1, 2 or 3 times daily, depending upon clearance rate. Accordingly, the desired dose may be presented in a single dose or as divided doses administered at appropriate intervals, for example two to four or more sub-doses per day.

The pharmaceutical compositions comprising the 3-aminopyrrolidone derivatives of formula I as above defined will contain, per dosage unit, e.g., capsule, tablet, powder injection, teaspoonful, suppository and the like from about 0.1 to about 500 mg of the active ingredient most preferably from 1 to 10 mg.

Optimal therapeutically effective doses to be administered may be readily determined by those skilled in the art and will vary, basically, with the strength of the preparation, with the mode of administration and with the advancement of the condition or disorder treated. In addition, factors associated with the particular subject being treated, including subject age, weight, diet and time of administration, will result in the need to adjust the dose to an appropriate therapeutically effective level.

The following examples further illustrate the invention.

Example 1

(S)-3-[4-(3-Fluorobenzyloxy)-benzylamino]-pyrrolidin-2-one

To a 2M solution of (S)-3-aminopyrrolidin-2-one (1.47 g, 14.6 mmol), prepared as described in Example 5, in anhydrous methanol 2.0 g of 3 Å molecular sieves and 0.77 g NaBH$_3$CN (12 mmol) were added; after 10 minutes, 3.4 g (14.8 mmol) of 4-(3-fluorobenzyloxy)benzaldeyde in 40 ml of anhydrous methanol were added. The reaction was carried out for 3 hours, then the mixture filtered, the solution was evaporated yielding a residue which was directly flash-chromatographed on silica gel (eluant: CHCl$_3$:CH$_3$OH:NH$_3$ (30%) 97:3:0.3, v:v:v) to give a white solid (3.4 g; 74%). The free base thus obtained was treated with a stoichiometric amount of methanesulfonic acid to give the title compound m.p. 140.5-143.5° C.

MS (ESI Pos Spray 3.5 kV; Skimmer 20 V; Probe 250° C.): 315 [MH$^+$]

Example 2

(S)-3-{N-[4-(3-Fluorobenzyloxy)-benzyl]-N-methyl}-amino-pyrrolidin-2-one 1.0 g (3.2 mmol) of (S)-3-[4-(3-fluorobenzyloxy)-benzylamino]-pyrrolidin-2-one was dissolved in 50 ml acetonitrile under inert conditions. 1.6 ml (20 mmol) of 37% formaldehyde and 0.29 g (4.6 mol) of sodium cyanoborohydride were added at room temperature. After 20 minutes glacial acetic acid was added until reaching a neutral pH value. The mixture was stirred for 40 minutes and then evaporated to dryness. After adding 40 ml of 2M potassium hydroxide the product was extracted with ethyl acetate, the organic layer was washed first with a 0.5 M KOH solution, then with water and brine. The organic layer was dried over Na$_2$SO$_4$, then filtered and evaporated to obtain a residue which was flash-chromatographed on silica gel (eluant: CHCl$_3$:CH$_3$OH:NH$_3$ (30%), 200:3:0.2, v:v:v) to give 0.73 g (70%) of a white solid m.p. 89-92° C.

MS (ESI Pos Spray 3.5 kV; Skimmer 20 V; Probe 250° C.): 329 [MH$^+$]

Example 3

(S)-3-[3,5-diMethyl-4-(4-trifluoromethyl-benzyloxy)-benzylamino]-pyrrolidin-2-one 2M solution of (S)-3-aminopyrrolidin-2-one (650 mg, 6.5 mmol), prepared as described in Example 5, in dry THF was added to a 1M solution of 3,5-dimethyl-4-(4-trifluoromethyl-benzyloxy)-benzaldehyde (2.2 g, 7.15 mmol), prepared as described in Example 6, in dry THF. To this mixture, a 2M solution of Ti(O-iPr)$_4$ (2.77 g, 9.75 mmol) in dry THF was added dropwise and the reaction mixture was stirred 12 hours at room temperature under nitrogen.

A 0.75M solution of sodium borohydride (690 mg, 18.2 mmol) in absolute ethanol was added and the resulting mixture was heated at 70° C. for 6 hours. After cooling, water (8 ml) was added and the resulting white precipitate was removed by filtration. The crude compound was purified using SCX cartridge (Strong Cation eXchange resin). The pure product was recovered by eluting with 3% ammonia solution in methanol. The title compound was obtained (2.24 g) after evaporating the solvent under vacuum with a yield of 88%.

MS (ESI Pos Spray 3.5 kV; Skimmer 20 V; Probe 250° C.): 393 [MH$^+$]

$^1$H-NMR (DMSO-d$_6$) δ: 7.7 (m, 5H), 7.0 (s, 2H), 4.9 (s, 2H), 3.68 (s, 2H), 3.15 (m, 3H), 2.22 (m, 7H), 1.7 (m, 1H).

Example 4

(S)-3-[4-(3,4-Dichloro-benzyloxy)-3-methyl-benzylamino]-pyrrolidin-2-one 2M solution of (S)-3-amino-pyrrolidin-2-one (650 mg, 6.5 mmol), prepared as described in Example 5, in dry THF was added to a 1M solution of 4-(3,4-dichloro-benzyloxy)-3-methyl-benzaldehyde (2.1 g, 7.15 mmol), prepared as described in Example 7, in dry THF. To this mixture, a 2M solution of Ti(O-iPR$_4$) (2.77 g, 9.75 mmol) in dry THF was added dropwise and the reaction mixture was stirred 12 hours at room temperature under nitrogen.

A 0.75M solution of sodium borohydride (690 mg, 18.2 mmol) in absolute ethanol was added and the resulting mixture was heated at 70° C. for 6 hours. After cooling, water (8 ml) was added and the resulting white precipitate was removed by filtration. The crude compound was purified using SCX cartridge (Strong Cation eXchange resin). The pure product was recovered by eluting with 3% ammonia solution in methanol. The title compound was obtained (2.18 g) after evaporating the solvent under vacuum with a yield of 89%.

MS (ESI Pos Spray 3.5 kV; Skimmer 20 V; Probe 250° C.): 378.9 [MH$^+$]

$^1$H-NMR (DMSO-d$_6$) δ: 7.72-7.68 (m, 3H), 7.45 (dd, 1H), 7.1 (m, 2H), 6.9 (dd, 1H), 5.15 (s, 2H), 3.65 (s, 2H), 3.15 (m, 3H), 2.20 (m, 4H), 1.68 (m, 1H).

Example 5

(S)-3-amino-pyrrolidin-2-one 5M solution of hexamethyldisilazane (108 ml, 523 mmol) in CH$_3$CN was added dropwise to a solution of (S)-2,4-diamino-butyric acid (10 g, 52.3 mmol) in CH$_3$CN (150 ml) at room temperature. The resulting mixture was refluxed for 30 hours. The crude reaction was poured into cold MeOH (400 ml), stirred at room temperature for 30 minutes and then evaporated under vacuum. The resulting solid was dissolved in $CH_2Cl_2$ (700 ml) and the insoluble residue was removed by filtration under vacuum.

The title compound was obtained (3.13 g) after evaporating the solution to dryness in a 60% yield.

Example 6

3,5-Dimethyl-4-(4-trifluoromethyl-benzyloxy)-benzaldehyde 0.5M solution of 1-bromomethyl-4-trifluoromethyl-benzene (1.9 g, 8.0 mmol) in DMF was added dropwise to a suspension of 4-hydroxy-3,5-dimethyl-benzaldehyde (930 mg, 7.3 mmol), $K_2CO_3$ (1.51 g, 11 mmol) and KI (120 mg, 0.73 mmol) in DMF (100 ml). The reaction mixture was stirred at 90° C. overnight. After cooling, the solid residue was filtered off and the solvent was evaporated under vacuum. The residue was dissolved in ethyl acetate and the organic layer washed twice with NaOH 1M, dried over $Na_2SO_4$ and evaporated to dryness. The residue was purified on silica gel, obtaining 2.24 g of the title compound in a quantitative yield.

Example 7

4-(3,4-diChloro-benzyloxy)-3-methyl-benzaldehyde 0.5M solution of 4-chloromethyl-1,2-dichloro-benzene (1.55 g, 8.0 mmol) in DMF was added dropwise to a suspension of 4-hydroxy-3-methyl-benzaldehyde (990 mg, 7.3 mmol), $K_2CO_3$ (1.51 g, 11 mmol) and KI (120 mg, 0.73 mmol) in DMF (100 ml). The reaction mixture was treated as described in Example 6. The residue was purified on silica gel, obtaining 2.15 g of the title compound in a quantitative yield.

Example 8

In Vitro Binding of $^3$H-Batrachotoxin in Rat Brain Membranes

Membrane preparations (P2 fraction) Male Wistar rats (Harlan, Italy—175-200 g) were sacrificed under light anaesthesia and brains were rapidly removed and cortex was dissected out, homogenized in 10 vol. of ice-cold 0.25 M sucrose buffer (50 mM Tris.HCl, pH 7.4). The crude homogenate was centrifuged at 3250 rpm for 10 min and the supernatant recovered. The pellet was homogenized and centrifuged again and the two supernatants were pooled and centrifuged at 14750 rpm for 10 min, +4° C. The resulting pellet was stored at −20° C. until use.

Binding assay. The pellet was resuspended in 50 mM Hepes buffer, pH 7.4 containing 0.8 mM $MgSO_4$, 5.4 mM KCl, 5.5 mM glucose and 130 mM choline using Polytron PT10. The binding assay was carried out in 0.25 ml final volume containing 50 µl of membrane preparation (ca 200 µg of protein), 50 µl of $^3$H-batrachotoxin ligand (10 nM), 50 µl of TTX (1 µM), 50 µl of scorpion toxin (37.5 µg/ml) and 50 µl of test compound or buffer or 300 µM of veratridine to determine non specific binding. The binding assay was performed at 37° C. for 30 min and stopped by rapid filtration under vacuum through Whatman GF/B glass fiber filters. Filters (pre-soaked with polyethylenimine 0.1%) were washed with 3×5 ml of ice-cold buffer and placed in picovials containing scintillation cocktail (Filter Count, Packard). Radioactivity bound was measured by liquid scintillation spectrometry at 45% efficiency.

Data analysis. The $IC_{50}$ was calculated from displacement curves by computer program LIGAND (McPherson, J. Pharmacol. Methods, 14, 213. 1985). The displacement curves were obtained using at least 9 concentrations, each in duplicate, covering a 100000 fold range.

Example 9

In Vitro Binding of $^3$H-Nitrendipine in Rat Brain Membranes

Membrane preparations Male Wistar rats (Harlan, Italy—175-200 g) were sacrificed under light anaesthesia and brains were rapidly removed and cortex was dissected out, homogenized in 10 vol. of ice-cold 50 mM Tris.HCl, pH 7.7 using Polytron PT10. The crude homogenate was centrifuged at 50000×g for 10 min. The pellet was homogenized and centrifuged twice in fresh buffer at 50000×g for 10 min, +4° C. The resulting pellet was stored at −20° C. until use.

Binding assay. The pellet was resuspended in 50 mM Tris HCl, pH 7.7 using Polytron PT10. The binding assay was carried out in 1 ml final volume containing 900 µL of membrane preparation (ca 700 µg of protein), 50 µl of $^3$H-nitrendipine (0.15 nM), and 50 µl of test compound or buffer or 1 µM of nifedipine to determine non specific binding. The binding assay was performed at 25° C. for 45 min and stopped by rapid filtration under vacuum through Whatman GF/B glass fiber filters. Filters were washed with 3×5 ml of ice-cold buffer and placed in picovials containing scintillation cocktail (Filter Count, Packard). Radioactivity bound was measured by liquid scintillation spectrometry at 45% efficiency.

Data analysis. The $IC_{50}$ was calculated from displacement curves by computer program LIGAND (McPherson, J. Pharmacol. Methods, 14, 213. 1985). The displacement curves were obtained using at least 9 concentrations, each in duplicate, covering a 100000 fold range.

Example 10

Calcium Influx Assay

IMR32 human neuroblastoma cells constitutively possess both L and N type channels. Under differentiating conditions, IMR32 preferentially express on the membrane surface N-type calcium channels. The remaining L-type calcium channels were blocked using the selective L type blocker, nifedipine. In these experimental conditions, only N type channels can be detected.

IMR32 cells were differentiated using 1 mM dibutyrril-cAMP and 2.5 µM bromodeoxyuridine for 8 days (4 times) in 225 $cm^2$ flask, then detached, seeded at 200,000 cells/well on 96 polilysine-coated plates and further incubated for 18-24 h in the presence of differentiating buffer before use.

The $Ca^{2+}$ Kit Assay (Molecular Devices), based on a fluorescent calcium indicator 485-535 nm wavelength, was used.

Differentiated cells were incubated with dye loading for 30 min at 37° C. then, nifedipine alone (1 µM) or in the presence of ω-conotoxin or test compounds were added for further 15 min.

The fluorescence (485-535 nm) was measured before and after (30-40 sec) the automated injection of 100 mM KCl depolarizing solution using a Victor plate reader (Perkin Elmer).

The inhibition curves were calculated from 5 concentrations, each in triplicate, and the $IC_{50}$ determined using a linear regression analysis.

Preferred compounds of general formula 1 inhibit N-type calcium channels with an $IC_{50}$ value less than 10 μM.

Example 11

Electrophysiological Assay

Experiments for the determination of the tonic block are carried out on isolated *Xenopus* oocytes expressing the Na channel Nav1.3. Currents are recorded using the two electrodes voltage clamp (TEVC) technique.

Oocytes Preparation:

The frog (*Xenopus Laevis*) is anesthesized in a solution with 3-aminobenzoic acid ethyl ester (1 g/l) and, after 25 minutes, it is placed on its back on an "iced-bed". The skin and the others tissues are cut, the ovarian lobes are pulled out and kept in ND96ØCa$^{2+}$ (NaCl 96 mM, KCl 2 mM, MgCl2 1 mM, Hepes 10 mM, pH 7.85 with NaOH).

After the removal of the oocytes, the muscle and the skin are sutured separately.

Ovarian lobes are reduced into clusters of 10/20 oocytes, put in tubes with collagenase solution (1 mg/ml) and kept in movement for about 1 h in an incubator.

At the end of this step, when the oocytes are well separated ones from the others, they are rinsed three times with ND96ØCa$^{2+}$ and three times with NDE (ND96ØCa$^{2+}$+CaCl 0.9 mM, MgCl2 0.9 mM, piruvate 2.5 mM, gentamicine 50 mg/l).

The oocytes obtained are at different stages of development. Only cells at stages V or VI are selected for RNA injection subsequent experiments.

The day after the preparation, the oocytes are injected (Drummond Nanoject) with 20 ng Nav1.3 cRNA and maintained in NDE.

Starting from 48 h after the mRNA injection whole cell currents are recorded using a two-microelectrode voltage clamp automated workstation.

Typical Microelectrodes have a resistance of 0.5 to 1 Mohm and are filled with KCl 3M.

Control bath solution contains (mM): NaCl 98, MgCl$_2$ 1, CaCl$_2$ 1.8, HEPES 5 (pH 7.6).

Compounds are prepared in stock solutions (20 mM) and dissolved to the final concentrations in the external bath solution.

Currents Recording:

The current/voltage (I/V) relationship for the Nav1.3 currents expressed in oocytes was first studied in order to determine the membrane potential evoking the maximal activation. Nav1.3 showed the max activation at 0 mV, that we used as test potential (Vtest) for tonic block studies.

The steady-state inactivation properties of the Nav1.3 currents were than studied in order to determine the membrane potentials for the resting state (Vrest) at which channel availability is maximal (Imax), and the membrane potential for the half maximal inactivation (V ½) producing half of the max current availability (I ½) respectively. This two voltage conditions were then used for the evaluation of the voltage dependence of the tonic block.

Finally a two-step protocol was used to determine the voltage dependence of the block of Nav1.3: the oocytes were clamped at −80 mV, the currents were activated by a 100 ms step pulse to 0 mV (Vtest) from a 3000 ms preconditioning potential at −80 mV (resting, Imax condition) and −40 mV (depolarized, I ½ condition), respectively.

Current amplitudes in the two conditions were recorded in the absence and in the presence of different concentrations of compound (washout was made in between) in order to determine the concentration—inhibition curves and $IC_{50}$ values for the tonic block in the depolarized (half max current availability) conditions.

Preferred compounds of general formula I inhibit Nav1.3 sodium channels with an $IC_{50}$ value lower than the reference sodium channel blocker ralfinamide.

Example 12

Mice Formalin Test

According to a modified protocol from Rosland et al., (1990) mice were injected subcutaneously (s.c.) with 20 μl of 2.7% solution of formalin into the plantar surface of left hindpaw and placed immediately into clear PVC observation chambers (23×12×13 cm). Pain behaviour was quantified by counting the cumulative licking time (s) of the injected paw. Measurements were taken during the early phase (0-5 min) and late phase (30-40 min) after formalin injection (Tjolsen et al. 1992).

The test compound was administered p.o. 15 min before formalin injection in a volume of 10 ml/kg body weight to groups of 10 mice per dose. Control group was treated with vehicle.

Example 13

Carragenan Model of Inflammation

Male Wistar rats of 175-200 grams were used.

The left hind paw was injected with 100 μl of carrageenan (2% w/v in saline). Compounds of the invention (30 mg/kg), indomethacin (5 mg/kg) or control vehicle (such as distilled water) were orally administered 1 h before carrageenan injection. The paw volume was measured with a plethysmometer (Ugo Basile) immediately before (basal) and 1, 2, 3, 4 and 5 h after the carrageenan injection.

The invention claimed is:

1. A compound of general formula I

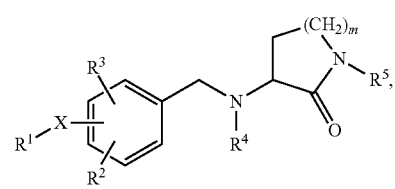

wherein
  m is an integer from 1 to 3
  X is methylene, oxygen, sulphur or a NR$^6$ group;
  R$^1$ is a straight or branched C$_1$-C$_8$ alkyl or C$_3$-C$_8$ alkenylene or C$_3$-C$_8$ alkynylene chain, optionally substituted with CF$_3$, phenyl, phenoxy or naphthyl or phenyl, the aromatic rings optionally substituted by one or more C$_1$-C$_4$ alkyl, halogens, trifluoromethyl, hydroxy or C$_1$-C$_4$ alkoxy groups;
  R$^2$, R$^3$ are independently hydrogen, a C$_1$-C$_3$ alkyl chain, halogen, trifluoromethyl, hydroxy or C$_1$-C$_4$ alkoxy groups;
  R$^4$, R$^5$, R$^6$ are independently hydrogen or C$_1$-C$_6$ alkyl; and
  the pharmaceutically acceptable salts thereof;
provided that:
  when R$^1$ is phenyl, benzyl, 2-phenethyl or 3-phenpropyl optionally and independently substituted on the phenyl ring by one or two $C_1$-$C_6$ alkyl, halogen, hydroxy, $C_1$-$C_4$ alkoxy or trifluoromethyl and X is oxygen, sulphur, methylene or —NH—, at least one of $R^2$ or $R^3$ is other than hydrogen;

if m is 3, $R^1$—X 4-benzyloxy, $R^2$, $R^4$ and $R^5$ hydrogen, then $R^3$ is other than 3-methoxy; and if m is 3, $R^1$—X 3-benzyloxy, $R^2$, $R^4$ and $R^5$ hydrogen, then $R^3$ is other than 4-methoxy.

2. A pharmaceutical composition containing the compound according to claim 1, or a pharmaceutically acceptable salt thereof, in admixture with a suitable carrier and/or diluent and optionally to other therapeutic agents.

* * * * *